United States Patent [19]

Liang et al.

[11] Patent Number: 5,599,672
[45] Date of Patent: Feb. 4, 1997

[54] METHOD OF DIFFERENTIAL DISPLAY OF EXPOSED MRNA BY RT/PCR

[75] Inventors: Peng Liang, Watertown; Arthur B. Pardee, Brookline; Cesario F. Bianchi, Boston, all of Mass.

[73] Assignees: Dana-Farber Cancer Institute, Inc., Boston; The President and Fellows of Harvard College, Cambridge, both of Mass.

[21] Appl. No.: 351,748

[22] Filed: Dec. 8, 1994

Related U.S. Application Data

[63] Continuation of Ser. No. 33,084, Mar. 11, 1993, abandoned, which is a continuation-in-part of Ser. No. 850,343, Mar. 11, 1992, Pat. No. 5,262,311.

[51] Int. Cl.$^6$ .......................... C07H 21/04; C12P 19/34; C12Q 1/68
[52] U.S. Cl. .......................... 435/6; 435/91.2; 536/24.33; 935/77; 935/78
[58] Field of Search .................. 435/6, 91.2; 536/24.33; 935/77, 78

[56] References Cited

U.S. PATENT DOCUMENTS 4,683,195  7/1987  Mullis et al. ............................. 435/91
5,104,792  4/1992  Silver .

FOREIGN PATENT DOCUMENTS

W/O 91/19816  12/1991  WIPO .
W/O 93/14217  7/1993  WIPO .

OTHER PUBLICATIONS

Loh et al., "Polymerase chain reaction with single-sided specificity: analysis of T cell receptor δ chain", Jan. 1989, Science, vol. 243, pp. 217–220.

Ghosh et al., "Cloning the cDNA encoding the AmbtV allergen from gaint ragweed (Ambrosia trifida) pollen", 1991, Gene, 101, pp. 231–238.

Schaefer et al., "Exclusive expression of Epstein–Barr virus nuclear antigen 1 in Burkitt lymphoma arises from a third promoter, distinct from the promoters used ing latently infected lymphocytes", Aug. 1991, Proc. Natl. Acad. Sci., USA, vol. 88, pp. 6550–6554.

Smith et al., "Complexity and sequence identification of 24 rat Vβ genes", Jul. 1, 1991, The Journal of Immunology, vol. 147, pp. 375–379.

(List continued on next page.)

*Primary Examiner*—Stephanie W. Zitomer
*Assistant Examiner*—Paul B. Tran
*Attorney, Agent, or Firm*—Choate, Hall & Stewart

[57] ABSTRACT

A method for isolating mRNAs as cDNAs employs a polymerase amplification method using at least two oligodeoxynucleotide primers. In one approach, the first primer contains sequence capable of hybridizing to a site immediately upstream of the first A ribonucleotide of the mRNA's polyA tail and the second primer contains arbitrary sequence. In another approach, the first primer contains sequence capable of hybridizing to a site including the mRNA's polyA signal sequence and the second primer contains arbitrary sequence. In another approach, the first primer contains arbitrary sequence and the second primer contains sequence capable of hybridizing to a site including the Kozak sequence. In another approach, the first primer contains a sequence that is substantially complementary to the sequence of a mRNA having a known sequence and the second primer contains arbitrary sequence. In another approach, the first primer contains arbitrary sequence and the second primer contains sequence that is substantially identical to the sequence of a mRNA having a known sequence. The first primer is used as a primer for reverse transcription of the mRNA and the resultant cDNA is amplified with a polymerase using both the first and second primers as a primer set.

23 Claims, 4 Drawing Sheets

```
5'-GCCACCATGGCTCTGAAGAGAATCCACAAGGACACCCATGAA...............
   Kozak
   ............................................................
   ............................................................
   ....................................GTTGCATTTACAACAAGAA TTTATCATCCAAATATTAACAGTAATGGCAGCATTTGTCTTGATATTCTACGGTCACCT - 3'
                                                    3'TGCCAGTGGA - 5'
                                                          AP-3
```

OTHER PUBLICATIONS

Xiao et al., "Charaterization of a full-length cDNA which codes for the human spermidine/spermine $N^1$-Acetyltansferase", Aug. 30, 1991, vol. 179, No. 1, pp. 407–415.

Zelent et al., "Differentially expressed isoforms of the mouse retinoic acid receptor β are generated by usage of two promoters and alternative splicing", 1991, The EMBO Journal, vol. 10, No,. 1, pp. 71–81.

Welsh et al., "Arbitrarily primed PCR fingerprinting of RNA", Nucleic Acids Research, vol. 20, No. 19, 1992.

He et al., "Molecular Cloning Of Androgen Receptors From Divergent Species With A Polymerase Chain Reaction Technique: Complete cDNA Sequence Of The Mouse Androgen Receptor And Isolation Of Andgrogen Receptor cDNA Probes From Dog, Guinea Pig and Clawed Frog", Biochemical and BioPhysical Research Communications, vol. 171, No. 2, Sep. 14, 1990.

Khan et al., "Efficient Double Stranded Sequencing Of cDNA Clones Containing Long Poly(A) Tails Using Anchored Poly(dT) Primers", Nucleic Acids Research, vol. 19, No. 7, Apr. 11, 1991.

Kocher et al., "Dynamics Of Mitochondrial DNA Evolution In Animals: Amplification And Sequencing With Conserved Primers", Proc. Natl. Acad. Sci., vol. 86, pp. 6196–6200, Aug. 1989.

Liang et al., "Differential Display and Cloning Of Messenger RNAs From Human Breast Cancer Versus Mammary Epithelial Cells", Cancer Research, vol. 52, pp. 6966–6968, Dec. 15, 1992.

Libert et al., "Selective Amplification And Cloning Of Four New Members Of The G Protein–Coupled Receptor Family", Science, vol. 244, pp. 569–572, May 5, 1989.

Osamu Ohara et al., "One–Sided Polymerase Chain Reaction: The Amplification of cDNA", Proc. Natl. Acad. Sci. USA, vol. 86, pp. 5673–5677, Aug. 1989.

Jamel Chelly et al., "Transcription of the Dystrophin Gene in Human Muscle and Non–Muscle Tissues", Nature, vol. 333, Jun. 30, 1988.

William T. Tse et al., "Reverse Transcription and Direct Amplification of Cellular RNA Transcripts by Taq Polymerase", Gene, vol. 88, No. 2, Apr. 16, 1990.

J. D. Fritz et al., "A Novel 3' Extension Technique Using Random Primers in RNA–PCR", Nucleic Acids Research, vol. 19, No. 13, Jul. 19, 1991.

Michael A. Frohman et al., "Rapid Production of Full–Length cDNAs from Rare Transcripts: Amplification Using a Single Gene–Specific Oligonucleotide Primer", Proc. Natl. Acad. Sci. USA, vol. 85, pp. 8998–9002, Dec. 1988.

T. D. Sargent, "Isolation of Differentially Expressed Genes", 1987, *Methods in Enzymology*, vol. 152, pp. 422–433.

M. Kozak, "An Analysis of Vertebrate mRNA Sequences: Intimations of Translational Control", Nov. 1991, *J. Cell Biology*, vol. 115, No. 4, pp. 887–903.

P. T. W. Cohen, "Cloning of Protein–Serine/Threonine Phosphatases", 1991, *Methods in Enzymology*, vol. 201, pp. 398–409.

A. F. Wilks, "Cloning Members of Protein–Tyrosine Kinase Family Using Polymerase Chain Reaction", 1991, *Methods in Enzymology*, vol. 200, pp. 533–547.

Welsh, Jr. et al. Nuc. Acids Res. 18(24):7213–7218, 1990.

Frohman, M. et al. Proc. Natl. Acad. Sci. 85:8998–9002, 1988.

Gilliand et al. in "PCR Protocols: A Guide to Methods and Applications", pp. 60–69, 1990.

Liang et al. Science 257(5072):967–971, 1992.

```
         10          20          30          40          50          60
CTTGATTGCC TCCTACAGCA GTTGCAGGCA CCTTTAGCTG TACCATGAAG TTCACAGTCC
─15        70          80          90         100         110         120
GGGATTGTGA CCCTAATACT GGAGTTCCAG ATGAAGATGG ATATGATGAT GAATATGTGC
        130         140         150         160         170         180
TGGAAGATCT TGAGGTAACT GTGTCTGATC ATATTCAGAA GATACTAAAA CCTAACTTCG
        190         200         210         220         230         240
CTGCTGCCTG GGAAGAGGTG GGAGGAGCAG CTGCGACAGA GCGTCCTCTT CACAGAGGGG
        250         260
TCCTGGGTGA AAAAAAAAAA
                 ─16
```

5'GCCACCATGGCTCTGAAGAGAATCCACAAGGACACCCATGAA..........
     Kozak
........
........
........
..........GTTGCATTTACAACAAGAA
........
........
........
TTTATCATCCAAATATTAACAGTAATGGCAGCATTTGTCTCTTGATATATTCTACGGTCACCT – 3'
                                      3' TGCCAGTGGA – 5'
                                            AP-3

FIG. 5

METHOD OF DIFFERENTIAL DISPLAY OF EXPOSED MRNA BY RT/PCR

This is a continuation of application Ser. No. 08/033,084 filed on Mar. 11, 1993 abandoned which is a continuation-in-part of U.S. Ser. No. 07/850,343, filed Mar. 11, 1992 and issued as U.S. Pat. No. 5,262,311 on Nov. 16, 1993.

BACKGROUND OF THE INVENTION

This invention relates to methods of detecting and cloning of individual mRNAs.

The activities of genes in cells are reflected in the kinds and quantities of their mRNA and protein species. Gene expression is crucial for processes such as aging, development, differentiation, metabolite production, progression of the cell cycle, and infectious or genetic or other disease states. Identification of the expressed mRNAs will be valuable for the elucidation of their molecular mechanisms, and for applications to the above processes.

Mammalian cells contain approximately 15,000 different mRNA sequences, however, each mRNA sequence is present at a different frequency within the cell. Generally, mRNAs are expressed at one of three levels. A few "abundant" mRNAs are present at about 10,000 copies per cell, about 3,000–4,000 "intermediate" mRNAs are present at 300–500 copies per cell, and about 11,000 "low-abundance" or "rare" mRNAs are present at approximately 15 copies per cell. The numerous genes that are represented by intermediate and low frequencies of their mRNAs can be cloned by a variety of well established techniques (see for example Sambrook et al., 1989, Molecular Cloning: A Laboratory Manual, Second Edition, Cold Spring Harbor Press, pp. 8.6–8.35).

If some knowledge of the gene sequence or protein is had, several direct cloning methods are available. However, if the identity of the desired gene is unknown one must be able to select or enrich for the desired gene product in order to identify the "unknown" gene without expending large amounts of time and resources.

The identification of unknown genes can often involve the use of subtractive or differential hybridization techniques. Subtractive hybridization techniques rely upon the use of very closely related cell populations, such that differences in gene expression will primarily represent the gene(s) of interest. A key element of the subtractive hybridization technique is the construction of a comprehensive complementary-DNA ("cDNA") library.

The construction of a comprehensive cDNA library is now a fairly routine procedure. PolyA mRNA is prepared from the desired cells and the first strand of the cDNA is synthesized using RNA-dependent DNA polymerase ("reverse transcriptase") and an oligodeoxynucleotide primer of 12 to 18 thymidine residues. The second strand of the cDNA is synthesized by one of several methods, the more efficient of which are commonly known as "replacement synthesis" and "primed synthesis".

Replacement synthesis involves the use of ribonuclease H ("RNAase H"), which cleaves the phosphodiester backbone of RNA that is in a RNA:DNA hybrid leaving a 3' hydroxyl and a 5' phosphate, to produce nicks and gaps in the mRNA strand, creating a series of RNA primers that are used by E. coli DNA polymerase I, or its "Klenow" fragment, to synthesize the second strand of the cDNA. This reaction is very efficient; however, the cDNAs produced most often lack the 5' terminus of the mRNA sequence.

Primed synthesis to generate the second cDNA strand is a general name for several methods which are more difficult than replacement synthesis yet clone the 5' terminal sequences with high efficiency. In general, after the synthesis of the first cDNA strand, the 3' end of the cDNA strand is extended with terminal transferase, an enzyme which adds a homopolymeric "tail" of deoxynucleotides, most commonly deoxycytidylate. This tail is then hybridized to a primer of oligodeoxyguanidylate or a synthetic fragment of DNA with an deoxyguanidylate tail and the second strand of the cDNA is synthesized using a DNA-dependent DNA polymerase.

The primed synthesis method is effective, but the method is laborious, and all resultant cDNA clones have a tract of deoxyguanidylate immediately upstream of the mRNA sequence. This deoxyguanidylate tract can interfere with transcription of the DNA in vitro or in vivo and can interfere with the sequencing of the clones by the Sanger dideoxynucleotide sequencing method.

Once both cDNA strands have been synthesized, the cDNA library is constructed by cloning the cDNAs into an appropriate plasmid or viral vector. In practice this can be done by directly ligating the blunt ends of the cDNAs into a vector which has been digested by a restriction endonuclease to produce blunt ends. Blunt end ligations are very inefficient, however, and this is not a common method of choice. A generally used method involves adding synthetic linkers or adapters containing restriction endonuclease recognition sequences to the ends of the cDNAs. The cDNAs can then be cloned into the desired vector at a greater efficiency.

Once a comprehensive cDNA library is constructed from a cell line, desired genes can be identified with the assistance of subtractive hybridization (see for example Sargent T. D., 1987, *Meth. Enzymol.*, Vol. 152, pp. 423–432; Lee et al., 1991, *Proc. Natl. Acad. Sci., USA*, Vol. 88, pp. 2825–2830). A general method for subtractive hybridization is as follows. The complementary strand of the cDNA is synthesized and radiolabelled. This single strand of cDNA can be made from polyA mRNA or from the existing cDNA library. The radiolabelled cDNA is hybridized to a large excess of mRNA from a closely related cell population. After hybridization the cDNA:mRNA hybrids are removed from the solution by chromatography on a hydroxylapatite column. The remaining "subtracted" radiolabelled cDNA can then be used to screen a cDNA or genomic DNA library of the same cell population.

Subtractive hybridization removes the majority of the genes expressed in both cell populations and thus enriches for genes which are present only in the desired cell population. However, if the expression of a particular mRNA sequence is only a few times more abundant in the desired cell population than the subtractive population it may not be possible to isolate the gene by subtractive hybridization.

SUMMARY OF THE INVENTION

We have discovered a method for identifying, isolating and cloning mRNAs as cDNAs using a polymerase amplification method that employs at least two oligodeoxynucleotide primers. In one approach, the first primer contains sequence capable of hybridizing to a site including sequence that is immediately upstream of the first A ribonucleotide of the mRNA's polyA tail and the second primer contains arbitrary sequence. In another approach, the first primer contains sequence capable of hybridizing to a site including the mRNA's polyA signal sequence and the second primer contains arbitrary sequence. In another approach, the first primer contains arbitrary sequence and the second primer contains sequence capable of hybridizing to a site including the mRNA's Kozak sequence. In another approach, the first primer contains a sequence that is substantially complementary to the sequence of a mRNA having a known sequence and the second primer contains arbitrary sequence. In another approach, the first primer contains arbitrary sequence and the second primer contains sequence that is substantially identical to the sequence of a mRNA having a known sequence. The first primer is used as a primer for reverse transcription of the mRNA and the resultant cDNA is amplified with a polymerase using both the first and second primers as a primer set.

Using this method with different pairs of the alterable primers, virtually any or all of the mRNAs from any cell type or any stage of the cell cycle, including very low abundance mRNAs, can be identified and isolated. Additionally a comparison of the mRNAs from closely related cells, which may be for example at different stages of development or different stages of the cell cycle, can show which of the mRNAs are constitutively expressed and which are differentially expressed, and their respective frequencies of expression.

The "first primer" or "first oligodeoxynucleotide" as used herein is defined as being the oligodeoxynucleotide primer that is used for the reverse transcription of the mRNA to make the first cDNA strand, and then is also used for amplification of the cDNA. The first primer can also be referred to as the 3' primer, as this primer will hybridize to the mRNA and will define the 3' end of the first cDNA strand. The "second primer" as used herein is defined as being the oligodeoxynucleotide primer that is used to make the second cDNA strand, and is also used for the amplification of the cDNA. The second primer may also be referred to as the 5' primer, as this primer will hybridize to the first cDNA strand and will define the 5' end of the second cDNA strand.

The "arbitrary" sequence of an oligodeoxynucleotide primer as used herein is defined as being based upon or subject to individual judgement or discretion. In some instances, the arbitrary sequence can be entirely random or partly random for one or more bases. In other instances the arbitrary sequence can be selected to contain a specific ratio of each deoxynucleotide, for example approximately equal proportions of each deoxynucleotide or predominantly one deoxynucleotide, or to not contain a specific deoxynucleotide. The arbitrary sequence can be selected to contain, or not to contain, a recognition site for specific restriction endonuclease. The arbitrary sequence can be selected to either contain a sequence that is substantially identical (at least 50% homologous) to a mRNA of known sequence or to not contain sequence from a mRNA of known sequence.

An oligodeoxynucleotide primer can be either "complementary" to a sequence or "substantially identical" to a sequence. As defined herein, a complementary oligodeoxynucleotide primer is a primer that contains a sequence which will hybridize to an mRNA, that is the bases are complementary to each other and a reverse transcriptase will be able to extend the primer to form a cDNA strand of the mRNA. As defined herein, a substantially identical primer is a primer that contains sequence which is the same as the sequence of an mRNA, that is greater than 50% identical, and the primer has the same orientation as an mRNA thus it will not hybridize to, or complement, an mRNA but such a primer can be used to hybridize to the first cDNA strand and can be extended by a polymerase to generate the second cDNA strand. The terms of art "hybridization" or "hybridize", as used herein, are defined to be the base pairing of an oligodeoxynucleotide primer with a mRNA or cDNA strand. The "conditions under which" an oligodeoxynucleotide hybridizes with an mRNA or a cDNA, as used herein, is defined to be temperature and buffer conditions (that are described later) under which the base pairing of the oligodeoxynucleotide primer with either an mRNA or a cDNA occurs and only a few mismatches (one or two) of the base pairing are permissible.

An oligonucleotide primer can contain a sequence that is known to be a "consensus sequence" of an mRNA of known sequence. As defined herein, a "consensus sequence" is a sequence that has been found in a gene family of proteins having a similar function or similar properties. The use of a primer that includes a consensus sequence may result in the cloning of additional members of a desired gene family.

The "preferred length" of an oligodeoxynucleotide primer, as used herein, is determined from the desired specificity of annealing and the number of oligodeoxynucleotides having the desired specificity that are required to hybridize to all the mRNAs in a cell. An oligodeoxynucleotide primer of 20 nucleotides is more specific than an oligodeoxynucleotide primer of 10 nucleotides; however, addition of each random nucleotide to an oligodeoxynucleotide primer increases by four the number of oligodeoxynucleotide primers required in order to hybridize to every mRNA in a cell.

In one aspect, in general, the invention features a method for identifying and isolating mRNAs by priming a preparation of mRNA for reverse transcription with a first oligodeoxynucleotide primer that contains sequence capable of hybridizing to a site including sequence that is immediately upstream of the first A ribonucleotide of the mRNA's polyA tail, and amplifying the cDNA by a polymerase amplification method using the first primer and a second oligodeoxynucleotide primer, for example a primer having arbitrary sequence, as a primer set.

In preferred embodiments, the first primer contains at least 1 nucleotide at the 3' end of the oligodeoxynucleotide that can hybridize to an mRNA sequence that is immediately upstream of the polyA tail, and contains at least 11 nucleotides at the 5' end that will hybridize to the polyA tail. The entire 3' oligodeoxynucleotide is preferably at least 13 nucleotides in length, and can be up to 20 nucleotides in length.

Most preferably, the first primer contains 2 nucleotides at the 3' end of the oligodeoxynucleotide that can hybridize to an mRNA sequence that is immediately upstream of the polyA tail. Preferably, the 2 polyA-non-complementary nucleotides are of the sequence VN, where V is deoxyadenylate ("dA"), deoxyguanylate ("dG"), or deoxycytidylate ("dC"), and N, the 3' terminal nucleotide, is dA, dG, dC, or deoxythymidylate ("dT"). Thus the sequence of a preferred first primer is 5'-TTTTTTTTTTTVN [Seq. ID. No. 1]. The use of 2 nucleotides can provide accurate positioning of the first primer at the junction between the mRNA and its polyA tail, as the properly aligned oligodeoxynucleotide:mRNA hybrids are more stable than improperly aligned hybrids, and thus the properly aligned hybrids will form and remain hybridized at higher temperatures. In preferred applications, the mRNA sample will be divided into at least twelve aliquots and one of the 12 possible VN sequences of the first primer will be used in each reaction to prime the reverse transcription of the mRNA. The use of an oligodeoxynucleotide with a single sequence will reduce the number of mRNAs to be analyzed in each sample by binding to a subset of the mRNAs, statistically 1/12th, thus simplifying the identification of the mRNAs in each sample.

In some embodiments, the 3' end of the first primer can have 1 nucleotide that can hybridize to an mRNA sequence that is immediately upstream of the polyA tail, and 12 nucleotides at the 5' end that will hybridize to the polyA tail, thus the primer will have the sequence 5'-TTTTTTTTTTTTV [Seq. ID. No. 2]. The use of a single non-polyA-complementary deoxynucleotide would decrease the number of oligodeoxynucleotides that are required to identify every mRNA to 3, however, the use of a single nucleotide to position the annealing of primer to the junction of the mRNA sequence and the polyA tail may result in a significant loss of specificity of the annealing and 2 non-polyA-complementary nucleotides are preferred.

In some embodiments, the 3' end of the first primer can have 3 or more nucleotides that can hybridize to an mRNA sequence that is immediately upstream of the polyA tail. The addition of each nucleotide to the 3' end will further increase the stability of properly aligned hybrids, and the sequence to hybridize to the polyA tail can be decreased by one nucleotide for each additional non-polyA-complementary nucleotide added. The use of such a first primer may not be practical for rapid screening of the mRNAs contained within a given cell line, as the use of a first primer with more than 2 nucleotides that hybridize to the mRNA immediately upstream of the polyA tail significantly increases the number of oligodeoxynucleotides required to identify every mRNA. For instance, the primer 5'-TTTTTTTTTTVNN [Seq. ID. No. 3] would require the use of 48 separate first primers in order to bind to every mRNA, and would significantly increase the number of reactions required to screen the mRNA from a given cell line. The use of oligodeoxynucleotides with a single random nucleotide in one position as a group of four can circumvent the problem of needing to set up 48 separate reactions in order to identify every mRNA. However as the non-polyA-complementary sequence became longer, it would quickly become necessary to increase the number of reactions required to identify every mRNA.

In preferred embodiments, the second primer is of arbitrary sequence and is at least 9 nucleotides in length. Preferably the second primer is at most 13 nucleotides in length and can be up to 20 nucleotides in length.

In another aspect, in general, the invention features a method for preparing and isolating mRNAs by priming a preparation of mRNA for reverse transcription with a first primer that contains a sequence capable of hybridizing to the polyadenylation signal sequence and at least 4 nucleotides that are positioned 5 ', or 3 ', or both of the polyadenylation signal sequence; this entire first primer is preferably at least 10 nucleotides in length, and can be up to 20 nucleotides in length. In one preferred embodiment the sequence 5'-NNTTTATTNN [Seq. ID. No. 4] can be chosen such that the sequence is 5'-GCTTTATTNC [Seq. ID. No. 5], and the four resultant primers are used together in a single reaction for the priming of the mRNA for reverse transcription. Once the first cDNA strand has been formed by reverse transcription then the first primer can be used with a second primer, for example and arbitrary sequence primer, for the amplification of the cDNA.

In one aspect, in general, the invention features a method for identifying and isolating mRNAs by priming a preparation of mRNA for reverse transcription with a first oligodeoxynucleotide primer to generate a first cDNA strand, and priming the preparation of the second cDNA strand with a second primer that contains sequence substantially identical to the Kozak sequence of mRNA, and amplifying the cDNA by a polymerase amplification method using the first and second primers as a primer set.

In preferred embodiments, the first and second primers are at least 9 deoxynucleotides in length, and are at most 13 nucleotides in length, and can be up to 20 nucleotides in length. Most preferably the first and second primers are 10 deoxynucleotides in length.

In preferred embodiments the sequence of the first primer is selected at random, or the first primer contains a selected arbitrary sequence, or the first primer contains a restriction endonuclease recognition sequence.

In preferred embodiments the sequence of the second primer that contains sequence substantially identical to the Kozak sequence of mRNA has the sequence NNNANNATGN [Seq. ID No. 6], or has the sequence NNNANNATGG [Seq. ID No. 7]. Where N is any of the four deoxynucleotides. Preferably, the second primer has the sequence GCCACCATGG [Seq. ID No. 8]. In some embodiments the first primer may further include a restriction endonuclease recognition sequence that is added to either the 5' or 3' end of the primer increasing the length of the primer by at least 5 nucleotides.

In another aspect, in general, the invention features a method for identifying and isolating mRNAs by priming a preparation of mRNA for reverse transcription with a first oligodeoxynucleotide primer that contains sequence that is substantially complementary to the sequence of a mRNA having a known sequence, and priming the preparation of the second cDNA strand with a second primer and, amplifying the cDNA by a polymerase amplification method using the first and second primers as a primer set.

In preferred embodiments, the first and second primers are at least 9 deoxynucleotides in length, and are at most 13 nucleotides in length, and can be up to 20 nucleotides in length. Most preferably the first and second primers are 10 deoxynucleotides in length.

In preferred embodiments the sequence of the first primer further includes a restriction endonuclease sequence, which may be included within the preferred 10 nucleotides of the primer or may be added to either the 3' or 5' end of the primer increasing the length of the oligodeoxynucleotide primer by at least 5 nucleotides.

In preferred embodiments the sequence of the second primer is selected at random, or the second primer contains a selected arbitrary sequence, or the second primer contains a restriction endonuclease recognition sequence.

In another aspect, in general, the invention features a method for identifying and isolating mRNAs by priming a preparation of mRNA for reverse transcription with a first oligodeoxynucleotide primer, and priming the preparation of the second cDNA strand with a second primer that contains sequence that is substantially identical to the sequence of a mRNA having a known sequence and, amplifying the cDNA by a polymerase amplification method using the first and second primers as a primer set.

In preferred embodiments, the first and second primers are at least 9 deoxynucleotides in length, and are at most 13 nucleotides in length, and can be up to 20 nucleotides in length. Most preferably the first and second primers are 10 deoxynucleotides in length.

In preferred embodiments the sequence of the first primer is selected at random, or the first primer contains a selected arbitrary sequence, or the first primer contains a restriction endonuclease recognition sequence.

In preferred embodiments the sequence of the second primer having a sequence that is substantially complementary to the sequence of an mRNA having a known sequence further includes a restriction endonuclease sequence, which may be included within the preferred 10 nucleotides of the primer or may be added to either the 3' or 5' end of the primer increasing the length of the oligodeoxynucleotide primer by at least 5 nucleotides.

In another aspect, in general, the invention features a method for identifying and isolating mRNAs by priming a preparation of mRNA for reverse transcription with a first oligodeoxynucleotide primer that contains sequence that is substantially complementary to the sequence of a mRNA having a known sequence, and priming the preparation of the second cDNA strand with a second primer that contains sequence that is substantially identical to the Kozak sequence of mRNA, and amplifying the cDNA by a polymerase amplification method using the first and second primers as a primer set.

In preferred embodiments, the first and second primers are at least 9 deoxynucleotides in length, and are at most 13 nucleotides in length, and can be up to 20 nucleotides in length. Most preferably the first and second primers are 10 deoxynucleotides in length.

In some preferred embodiments of each of the general aspects of the invention, the amplified cDNAs are separated and then the desired cDNAs are reamplified using a polymerase amplification reaction and the first and second oligodeoxynucleotide primers.

In preferred embodiments of each of the general aspects of the invention, a set of first and second oligodeoxynucleotide primers can be used, consisting of more than one of each primer. In some embodiments more than one of the first primer will be included in the reverse transcription reaction and more than one each of the first and second primers will be included in the amplification reactions. The use of more than one of each primer will increase the number of mRNAs identified in each reaction, and the total number of primers to be used will be determined based upon the desired method of separating the cDNAs such that it remains possible to fully isolate each individual cDNA. In preferred embodiments a few hundred cDNAs can be isolated and identified using denaturing polyacrylamide gel electrophoresis.

The method according to the invention is a significant advance over current cloning techniques that utilize subtractive hybridization. In one aspect, the method according to the invention enables the genes which are altered in their frequency of expression, as well as of mRNAs which are constitutively and differentially expressed, to be identified by simple visual inspection and isolated. In another aspect the method according to the invention provides specific oligodeoxynucleotide primers for amplification of the desired mRNA as cDNA and makes unnecessary an intermediary step of adding a homopolymeric tail to the first cDNA strand for priming of the second cDNA strand and thereby avoiding any interference from the homopolymeric tail with subsequent analysis of the isolated gene and its product. In another aspect the method according to the invention allows the cloning and sequencing of selected mRNAs, so that the investigator may determine the relative desirability of the gene prior to screening a comprehensive cDNA library for the full length gene product.

DESCRIPTION OF THE PREFERRED EMBODIMENTS

Drawings FIG. 1 is a schematic representation of the method according to the invention.

FIG. 2 is the sequence of the 3' end of the N1 gene from normal mouse fibroblast cells (A31) [Seq. ID. No. 9].

FIG. 5 is a partial sequence of the 5' end of a clone, K1, that was cloned from the A1-5 cell line that was cultured at the non-permissive temperature and then shifted to the permissive temperature (32.5° C.) for 24 h prior to the preparation of the mRNA. The A1-5 cell line is a rat primary embryo cell line that has been doubly transformed with ras and a temperature sensitive mutation of $P^{53}$ ("$P^{53ts}$").

GENERAL DESCRIPTION, DEVELOPMENT OF THE METHOD

By way of illustration a description of examples of the method of the invention follows, with a description by way of guidance of how the particular illustrative examples were developed.

It is important for operation of the method that the length of the oligodeoxynucleotide be appropriate for specific hybridization to mRNA. In order to obtain specific hybridization, whether for conventional cloning methods or PCR, oligodeoxynucleotides are usually chosen to be 20 or more nucleotides in length. The use of long oligodeoxynucleotides in this instance would decrease the number of mRNAs identified during each trial and would greatly increase the number of oligodeoxynucleotides required to identify every mRNA. Recently, it was demonstrated that 9–10 nucleotide primers can be used for DNA polymorphism analysis by PCR (Williams et al., 1991, *Nuc. Acids Res.*, Vol. 18, pp. 6531–6535).

The plasmid containing the cloned murine thymidine kinase gene ("TK cDNA plasmid") was used as a model template to determine the required lengths of oligodeoxynucleotides for specific hybridization to a mRNA, and for the production of specific PCR products. The oligodeoxynucleotide primer chosen to hybridize internally in the mRNA was varied between 6 and 13 nucleotides in length, and the oligodeoxynucleotide primer chosen to hybridize at the upstream end of the polyA tail was varied between 7 and 14 nucleotides in length. After numerous trials with different sets and lengths of primers, it was determined that the annealing temperature of 42° C. is optimal for product specificity and the internally hybridizing oligodeoxynucleotide should be at least 9 nucleotides in length and a oligodeoxynucleotide that is at least 13 nucleotides in length is required to bind to the upstream end of the polyA tail.

Figure 1:
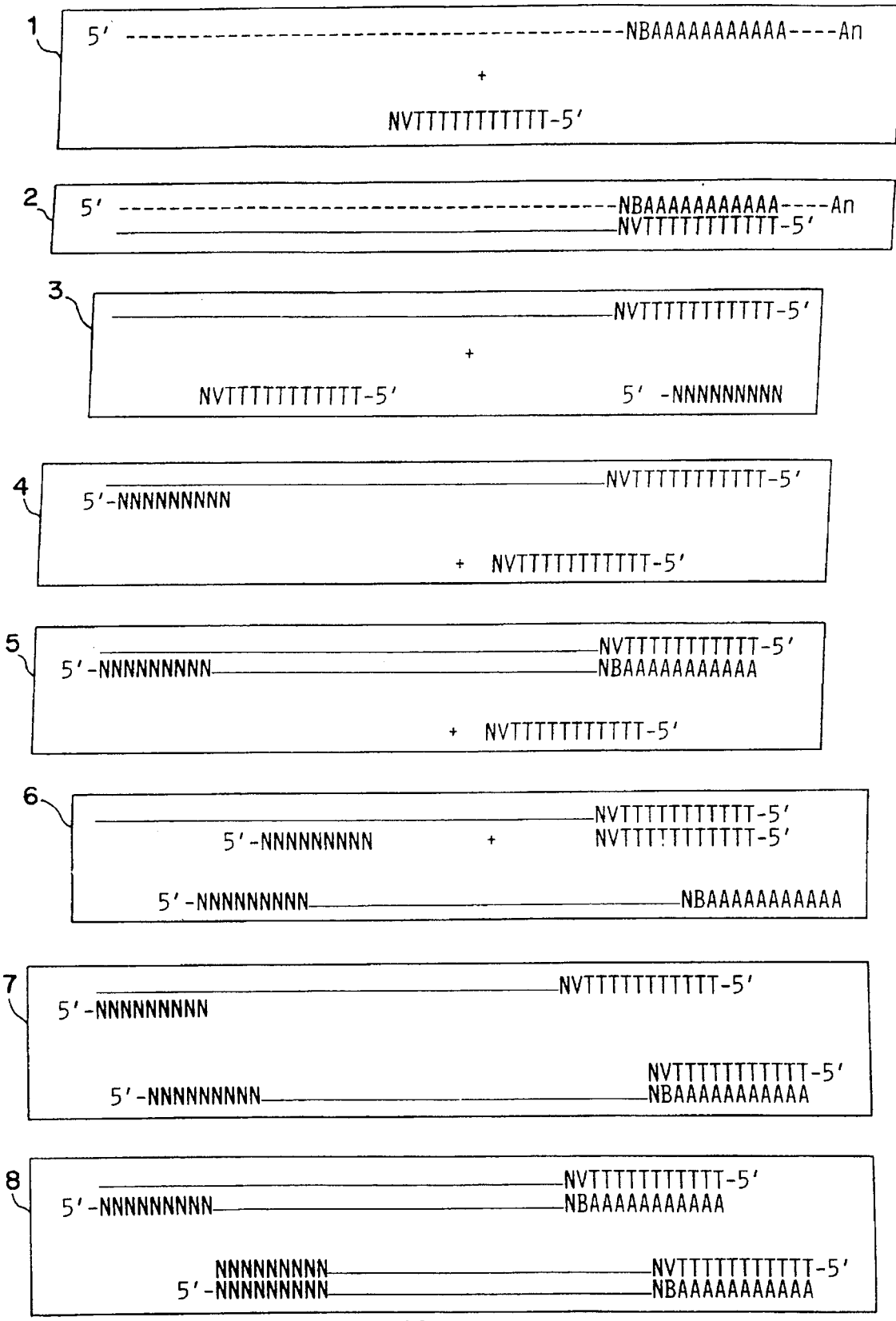

With reference now to FIG. 1, the method according to the invention is depicted schematically. The mRNAs are mixed with the first primer, for example TTTTTTTTTTTVN [Seq. ID. No. 2] ($T_{11}VN$) 1, and reverse transcribed 2 to make the first cDNA strand. The cDNA is amplified as follows. The first cDNA strand is added to the second primer and the first primer and the polymerase in the standard buffer with the appropriate concentrations of nucleotides and the components are heated to 94° C. to denature the mRNA:cDNA hybrid 3, the temperature is reduced to 42° C. to allow the second primer to anneal 4, and then the temperature is increased to 72° C. to allow the polymerase to extend the second primer 5. The cycling of the temperature is then repeated 6, 7, 8, to begin the amplification of the sequences which are hybridized by the first and second primers. The temperature is cycled until the desired number of copies of each sequence have been made.

As is well known in the art, this amplification method can be accomplished using thermal stable polymerase or a polymerase that is not thermal stable. When a polymerase that is not thermal stable is used, fresh polymerase must be added after the annealing of the primers to the templates at the start of the elongation or extending step, and the extension step must be carried out at a temperature that is permissible for the chosen polymerase.

The following examples of the method of the invention are presented for illustrative purposes only. As will be appreciated, the method according to the invention can be used for the isolation of polyA mRNA from any source and can be used to isolate genes expressed either differentially or constitutively at any level, from rare to abundant.

EXAMPLE 1

Experimentation with the conditions required for accurate and reproducible results by PCR were conducted with the TK cDNA plasmid and a single set of oligodeoxynucleotide primers; the sequence TTTTTTTTTTTCA ("$T_{11}CA$") [Seq. ID. No. 10] was chosen to hybridize to the upstream end of the polyA tail and the sequence CTTGATTGCC ("Ltk3") [Seq. ID. No. 11] was chosen to hybridize 288 base pairs ("bp") upstream of the polyA tail. The expected fragment size using these two primers is 299 bp.

PCR was conducted under standard buffer conditions well known in the art with 10 ng TK cDNA plasmid (buffer and polymerase are available from Perkin Elmer-Cetus). The standard conditions were altered in that the primers were used at concentrations of 2.5 µM $T_{11}CA$, 0.5 µM Ltk3, instead of 1 µM of each primer. The concentration of the nucleotides ("dNTPs") was also varied over a 100 fold range, from the standard 200 µM to 2 µM. The PCR parameters were 40 cycles of a denaturing step for 30 seconds at 94° C., an annealing step for 1 minute at 42° C., and an extension step for 30 seconds at 72° C. Significant amounts of non-specific PCR products were observed when the dNTP concentration was 200 µM, concentrations of dNTPs at or below 20 µM yielded specifically amplified PCR products. The specificity of the PCR products was verified by restriction endonuclease digest of the amplified DNA, which yielded the expected sizes of restriction fragments. In some instances it was found that the use of up to 5 fold more of the first primer than the second primer also functioned to increase the specificity of the product. Lowering the dNTP concentration to 2 µM allowed the labelling of the PCR products to a high specific activity with [α-$^{35}$S] dATP, 0.5 µM [α-$^{35}$S] dATP (Sp. Act. 1200 Ci/mmol), which is necessary for distinguishing the PCR products when resolved by high resolution denaturing polyacrylamide gel electrophoresis, in this case a DNA sequencing gel.

EXAMPLE 2

The PCR method of amplification with short oligodeoxynucleotide primers was then used to detect a subset of mRNAs in mammalian cells. Total RNAs and mRNAs were prepared from mouse fibroblasts cells which were either growing normally, "cycling", or serum starved, "quiescent".

The RNAs and mRNAs were reverse transcribed with $T_{11}CA$ as the primer. The $T_{11}CA$ primer was annealed to the mRNA by heating the mRNA and primer together to 65° C. and allowing the mixture to gradually cool to 35° C. The reverse transcription reaction was carried out with Moloney murine leukemia virus reverse transcriptase at 35° C. The resultant cDNAs were amplified by PCR in the presence of $T_{11}CA$ and Ltk3, as described in Example 1, using 2 µM dNTPs. The use of the $T_{11}CA$ and Ltk3 primers allowed the TK mRNA to be used as an internal control for differential expression of a rare mRNA transcript; TK mRNA is present at approximately 30 copies per cell. The DNA sequencing gel revealed 50 to 100 amplified mRNAs in the size range which is optimal for further analysis, between 100 to 500 nucleotides. The patterns of the mRNA species observed in cycling and quiescent cells were very similar as expected, though some differences were apparent. Notably, the TK gene mRNA, which is expressed during G1 and S phase, was found only in the RNA preparations from cycling cells, as expected, thus demonstrating the ability of this method to separate and isolate rare mRNA species such as TK.

EXAMPLE 3

The expression of mRNAs in normal and tumorigenic mouse fibroblast cells was also compared using the $T_{11}CA$ and Ltk3 primers for the PCR amplification. The mRNA was reverse transcribed using $T_{11}CA$ as the primer and the resultant cDNA was amplified by PCR using 2 µM dNTPs and the PCR parameters described above. The PCR products were separated on a DNA sequencing gel. The TK mRNA was present at the same level in both the normal and tumorigenic mRNA preparations, as expected, and provided a good internal control to demonstrate the representation of rare mRNA species. Several other bands were present in one preparation and not in the other, with a few bands present in only the mRNA from normal cells and a few bands present only in the mRNA from the tumorigenic cells; and some bands were expressed to different levels in the normal and tumorigenic cells. Thus, the method according to the invention can be used to identify genes which are normally continuously expressed (constitutive), and differentially expressed, suppressed, or otherwise altered in their level of expression.

Cloning of the mRNA identified in Example 3

Three cDNAs that are, the TK cDNA, one cDNA expressed only in normal cells ("N1"), and one cDNA expressed only in tumorigenic cells ("T1"), were recovered from the DNA sequencing gel by electroelution, ethanol precipitated to remove the urea and other contaminants, and reamplified by PCR, in two consecutive PCR amplifications of 40 cycles each, with the primers $T_{11}CA$ and Ltk3 in the presence of 20 µM dNTPs to achieve optimal yield without compromising the specificity. The reamplified PCR products were confirmed to have the appropriate sizes and primer dependencies as an additional control the reamplified TK cDNA was digested with two separate restriction endonucleases and the digestion products were also confirmed to be of the correct size.

Figures 2, 3:
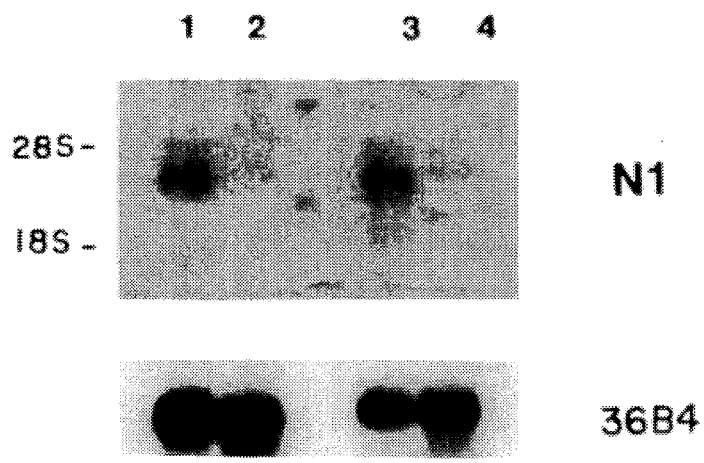
FIG. 3 is the Northern blot of the N1 sequence on total cellular RNA from normal and tumorigenic mouse fibroblast cells.

The reamplified N1 was cloned with the TA cloning system, Invitrogen Inc., into the plasmid pCR1000 and sequenced. With reference now to FIG. 2, the nucleotide sequence clearly shows the N1 fragment to be flanked by the underlined Ltk3 primer 15 at the 5' end and the underlined $T_{11}CA$ primer 16 at the 3' end as expected.

A Northern analysis of total cellular RNA using a radiolabelled N1 probe reconfirmed that the N1 mRNA was only present in the normal mouse fibroblast cells, and not in the tumorigenic mouse fibroblast cells. With reference now to FIG. 3, the probe used to detect the mRNA is labelled to the right of the figure, and the size of the N1 mRNA can be estimated from the 28S and 18S markers depicted to the left of the figure. The N1 mRNA is present at low abundance in both exponentially growing and quiescent normal cells, lanes 1 and 3, and is absent from both exponentially growing or quiescent tumorigenic cells, lanes 2 and 4. As a control, the same Northern blot was reprobed with a radiolabelled probe for 36B4, a gene that is expressed in both normal and tumorigenic cells, to demonstrate that equal amounts of mRNA, lanes 1–4, were present on the Northern blot.

EXAMPLE 4

The comparison of the expression of mRNAs in three cell lines, with one cell line examined under two different culture conditions, was conducted. The cell lines were a primary rat embryo fibroblast cell line ("REF"), the REF cell line that has been doubly transformed with ras and a mutant of $P^{53}$ ("T101-4"), and the REF cell line that has been doubly transformed with ras and a temperature sensitive mutation of $P^{53}$ ("A1-5"). The A1-5 cell line was cultured at the non-permissive temperature of 37° C. for preparation of mRNA, and cultured at the permissive temperature by first culturing the cells at 37° C. and then shifting the cells to 32.5° C. for 24 h prior to the preparation of the mRNA. The method of the invention was conducted using the primers "Kozak" and one of five arbitrary sequence primers, "AP-1, AP-2, AP-3, AP-4, or AP-5", as the second and first primers, respectively.

The sequence of the "Kozak" primer was chosen based upon the published consensus sequence for the translation start site consensus sequence of mRNAs (Kozak, 1991, *Jour. Cell Biology*, Vol. 115, pp. 887–903). A degenerate Kozak primer having sequences substantially identical to the translation start site consensus sequence were used simultaneously, these sequences were 5'-GCCRCCATGG [Seq. ID No. 12], in which the R is dA or dG and thus the oligodeoxynucleotide primer has only one of the given nucleotides which results in a mixture of primers.

The sequence of the five arbitrary primers was a follows: AP-1 had the sequence 5'-AGCCAGCGAA [Seq. ID. No. 13]; AP-2 had the sequence 5'-GACCGCTTGT [Seq. ID. No. 14]; AP-3 had the sequence 5'-AGGTGACCGT [Seq. ID. No. 15]; AP-4 had the sequence 5'-GGTACTCCAC [Seq. ID. No. 16]; and AP-5 had the sequence 5'-GTTGCGATCC [Seq. ID. No. 17]. These arbitrary sequence primers were chosen arbitrarily. In general each arbitrary sequence primer was chosen to have a GC content of 50–70%.

The mRNA was reverse transcribed using one of the AP primers, as the first primer, and the resultant first cDNA strand was amplified in the presence of both primers, the AP primer and the degenerate Kozak primer, by PCR using 2 µM NTPs and the PCR parameters described above. The PCR products were separated on a DNA sequencing gel. At least 50–100 amplified cDNA bands were present in each of the cell lines tested, and some bands were expressed to different levels in the different cell lines.

Figure 4:
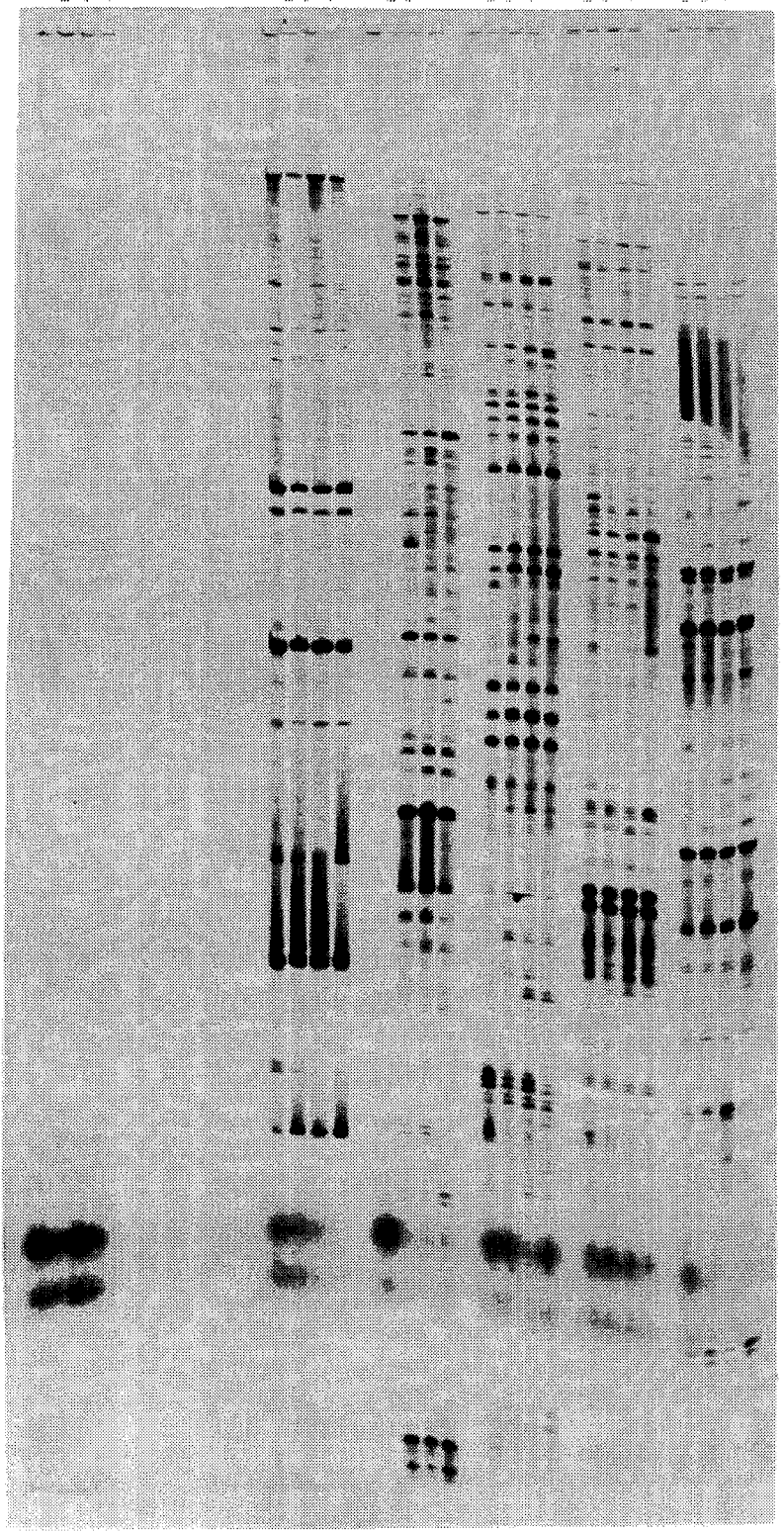
FIG. 4 is a sequencing gel showing the results of amplification for mRNA prepared from four sources (lanes 1–4), using the Kozak primer alone, the AP-1 primer alone, the Kozak and AP-1 primers, the Kozak and AP-2 primers, the Kozak and AP-3 primers, the Kozak and AP-4 primers and the Kozak and AP-5 primers. This gel will be more fully described later.

With reference now to FIG. 4, the primer sets used for each reaction are shown at the top of the Fig. along the line marked Primers. As a control a reaction was conducted using the primers in the absence of mRNA and using Ap-1 with mRNA in the absence of the Kozak primer. No cDNA was generated by the primers in the absence of mRNA or by the arbitrary primer alone, thus demonstrating that mRNA is required for the amplification and that both primers were required to amplify an mRNA into a cDNA. The cDNA products of the amplification were loaded in the same order across the gel, thus the REF cell line is shown in each of lanes 1, cell line T101-4 is shown in each of lanes 2, cell line A1-5 cultured at 37° C. is shown in each of lanes 3, and cell line A1-5 cultured at 32.5° C. is shown in each of lanes 4. Each pair of rpimers reulted in the amplification of a different set of mRNAs from the cell lines. The reactions which were conducted using the Kozak primer and any of primers AP-1, AP-2, AP-4, or AP-5 as a primer set resulted in the amplification of the same cDNA pattern from each of cell lines REF, T101-4, A1-5 cultured at 37° C. and A1-5 cultured at 32.5° C. The amplification of mRNA from each cell line and temperature using the Kozak degenerate primer and the AP-3 primer resulted in the finding of one band in particular which was present in the mRNA prepared from the A1-5 cell line when cultured at 32.5° C. for 24 h, and not in any of the other mRNA preparations, as can be seen in FIG. 4 designated as K1. Thus the method according to the invention may be used to identify genes which are differentially expressed in mutant cell lines.

Cloning of the mRNA identified in Example 4

The cDNA ("K1") that was expressed only in the A1-5 cell line when cultured at 32.5° C. was recovered from the DNA sequencing gel and reamplified using the primers Kozak and AP-3 as described above. The reamplified $K_1$ cDNA was confirmed to have the appropriate size of approximately 450 bp, and was cloned with the TA cloning system, Invitrogen Inc., into the vector pCRII (Invitrogen, Inc.) according to the manufacturers instructions, and sequenced. With reference now to FIG. 5, the nucleotide sequence clearly shows the K1 clone to be flanked by the underlined Kozak primer 20 at the 5' end and the underlined AP-3 primer 21 at the 3' end as expected. The 5' end of this partial cDNA is identified in Seq. ID No. 18, and the 3' end of this cDNA is identified in Seq. ID No. 19. This partial sequence is an open reading frame, and a search of the gene databases EMBO and Genbank has revealed the translated amino acid sequence from the 3' portion of K1 to be homologous to the ubiquitin conjugating enzyme family (UBC enzyme). The translated amino acid sequence of the 3' portion of K1 is 100% identical to a UBC enzyme from *D. melanogaster*; and 75% identical to the UBC-4 enzyme and 79% identical to the UBC-5 enzyme from the yeast *S. saccharomyces*; and 75% identical to the UBC enzyme from *Arabidopsis thaliana*. The K1 clone may contain the actual 5' end of this gene, otherwise the Kozak primer hybridized just after the 5' end. This result demonstrates that the method according to the invention can be used to clone the 5' coding sequence of a gene.

Use of the Invention

The method according to the invention can be used to identify, isolate and clone mRNAs from any number of sources. The method provides for the identification of desirable mRNAs by simple visual inspection after separation, and can be used for investigative research, industrial and medical applications.

For instance, the reamplified cDNAs can be sequenced, or used to screen a DNA library in order to obtain the full length gene. Once the sequence of the cDNA is known, amino acid peptides can be made from the translated protein sequence and used to raise antibodies. These antibodies can be used for further research of the gene product and its function, or can be applied to medical diagnosis and prognosis. The reamplified cDNAs can be cloned into an appropriate vector for further propagation, or cloned into an appropriate expression vector in order to be expressed, either in vitro or in vivo. The cDNAs which have been cloned into expression vectors can be used in industrial situations for overproduction of the protein product. In other applications the reamplified cDNAs or their respective clones will be used as probes for in situ hybridization. Such probes can also be used for the diagnosis or prognosis of disease.

OTHER EMBODIMENTS

Other embodiments are within the following claims.

The length of the oligodeoxynucleotide can be varied dependent upon the annealing temperature chosen. In the preferred embodiments the temperature was chosen to be 42° C. and the oligonucleotide primers were chosen to be at least 9 nucleotides in length. If the annealing temperature were decreased to 35° C. then the oligonucleotide lengths can be decreased to at least 6 nucleotides in length.

The cDNA could be radiolabelled with radioactive nucleotides other than $^{35}$S, such as $^{32}$P and $^{33}$P. When desired, non-radioactive imaging methods can also be applied to the method according to the invention.

The amplification of the cDNA could be accomplished by a temperature cycling polymerase chain reaction, as was described, using a heat stable DNA polymerase for the repetitive copying of the cDNA while cycling the temperature for continuous rounds of denaturation, annealing and extension. Or the amplification could be accomplished by an isothermal DNA amplification method (Walker et al., 1992, *Proc. Natl. Acad. Sci.*, Vol. 89, pp. 392–396). The isothermal amplification method would be adapted to use for amplifying cDNA by including an appropriate restriction endonuclease sequence, one that will be nicked at hemiphosphorothioate recognition sites and whose recognition site can be regenerated during synthesis with $\alpha^{35}$S labelled dNTPs.

Proteins having similar function or similar functional domains are often referred to as being part of a gene family. Many such proteins have been cloned and identified to contain consensus sequences which are highly conserved amongst the members of the family. This conservation of sequence can be used to design oligodeoxynucleotide primers for the cloning of new members, or related members, of a family. Using the method of the invention the mRNA from a cell can be reverse transcribed, and a cDNA could be amplified using at least one primer that has a sequence substantially identical to the sequence of a mRNA of known sequence. Consensus sequences for at least the following families and functional domains have been described in the literature: protein tyrosine kinases (Hanks et al., 1991, *Methods on Enzymology*, Vol. 200, pp. 38–81; Wilks, 1991, *Methods in Enzymology*, Vol. 200, pp. 533–546); homeobox genes; zinc-finger DNA binding proteins (Miller et al., 1985, *EMBO Jour.*, Vol. 4, pp. 1609–1614); receptor proteins; the signal peptide sequence of secreted proteins; proteins that localize to the nucleus (Guiochon-Mantel et al., 1989, Vol. 57, pp. 1147–1154); serine proteases; inhibitors of serine proteases; cytokines; the SH2 and SH3 domains that have been described in tyrosine kinases and other proteins (Pawson et al., 1992, *Cell*, Vol 71, pp. 359–362); serine/threonine and tyrosine phosphatases (Cohen, 1991, *Methods in Enzymology*, Vol. 201, pp. 398–408); cyclins and cyclin-dependent protein kinases (CDKs) (see for ex., Keyomarsi et al., 1993, *Proc. Natl. Acad. Sci., USA*, Vol. 90, pp. 1112–1116).

Primers for any consensus sequence can readily be designed based upon the codon usage of the amino acids. The incorporation of degeneracy at one or more sites allows the designing of a primer which will hybridize to a high percentage, greater than 50%, of the mRNAs containing the desired consensus sequence.

Primers for use in the method according to the invention could be designed based upon the consensus sequence of the zinc finger DNA binding proteins, for example, based upon the amino acid consensus sequence of the proteins PYVC [SEQ. ID. No. 22]. Useful primers for the cloning of further members of this family can have the following sequences: 5'-GTAYGCNTGT [Seq. ID. No. 20] or 5'-GTAYGCNTGC [Seq. ID. No. 21], in which the Y refers to the deoxynucleotides dT or dC for which the primer is degenerate at this position, and the N refers to inosine ("I"). The base inosine can pair with all of the other bases, and was chosen for this position of the oligodeoxynucleotide as the codon for valine "V" is highly degenerate in this position. The described oligodeoxynucleotide primers as used will be a mixture of 5'-GTATGCITGT [SEQ. ID. No. 23] and 5'-GTACGCITGT [Seq. ID. No. 24] or a mixture of 5'-GTATGCITGC [Seq. ID. No. 25] and 5'-GTACGCITGC [Seq. ID. No. 26].

We claim:

1. A method of comparing the presence or level of individual mRNA molecules in two or more nucleic acid samples, comprising the steps of:

providing a first nucleic acid sample including mRNA molecules;

providing a second nucleic acid sample including mRNA molecules;

contacting each of said first nucleic acid sample and said second nucleic acid sample with a first oligodeoxynucleotide primer that hybridizes to a first site in mRNAs in said first and second nucleic acid samples;

reverse transcribing said mRNAs to which said first primer hybridizes to produce a first population of DNA strands that are complementary to said mRNAs in said first nucleic acid sample to which said first primer hybridizes, and a second population of DNA strands that are complementary to said mRNAs in said second nucleic acid sample to which said first primer hybridizes;

contacting said first and second populations of DNA strands with a second oligodeoxynucleotide primer that hybridizes to a second site in said first and second populations of DNA strands, which second site includes NNNRNNATGN (SEQ ID NO:27), said contacting being performed under conditions in which said second primer hybridizes with at least some of the DNA strands in said first and second populations;

extending said second primer to produce a third population of DNA strands that are complementary to the DNA strands in said first population to which said second primer hybridizes, and a fourth population of DNA strands that are complementary to the DNA strands in said second population to which said second primer hybridizes;

amplifying portions of the DNA strands in said first and third populations of DNA strands with said first and second primers to produce a first population of amplification products;

amplifying portions of the DNA strands in said second and fourth populations of DNA strands with said first and second primers to produce a second population of amplification products;

comparing the presence or level of individual amplification products in said first and second populations of amplification products.

2. The method of claim 1 wherein said first nucleic acid sample comprises mRNAs expressed in a first cell and said second nucleic acid sample consists of mRNAs expressed in a second cell.

3. The method of claim 1 wherein said first nucleic acid sample comprises mRNAs expressed in a cell at a first developmental stage and said second nucleic acid sample comprises mRNAs expressed in said cell at a second developmental stage.

4. The method of claim 1 wherein said first nucleic acid sample comprises mRNAs expressed in a tumorigenic cell and said second nucleic acid sample comprises mRNAs expressed in a normal cell.

5. The method of claim 1 wherein said first primer has an arbitrary nucleotide sequence and is at least 6 nucleotides in length.

6. The method of claim 5 wherein said first primer is about 9–10 nucleotides in length.

7. The method of claim 5 wherein said first primer has a GC content within the range of about 50–70%.

8. The method of claim 1 wherein the nucleotide sequence of said first or said second primer includes a sequence that is recognized by a restriction endonuclease.

9. The method of claim 1 wherein the nucleotide sequence of said first primer includes a sequence substantially complementary to a consensus sequence found in a gene family.

10. The method of claim 1 wherein the nucleotide sequence of said first primer includes a sequence substantially complementary to a sequence found in an mRNA of known sequence.

11. The method of claim 1 wherein at least one of said first and second primers comprises a plurality of oligodeoxynucleotides.

12. The method of claim 1 wherein individual oligodeoxynucleotide molecules in said plurality of oligodeoxynucleotides have the same nucleotide sequence.

13. The method of claim 1 wherein individual oligodeoxynucleotide molecules in said plurality of oligodeoxynucleotides have different nucleotide sequences.

14. The method of claim 1 wherein the amplifying steps each comprise performing a polymerase chain reaction in which the concentration of dNTPs is at or below approximately 20 μM.

15. The method of claim 1 wherein the amplifying steps each comprise performing a polymerase chain reaction in which the concentration of dNTPs is approximately 2 μM.

16. The method of claim 1 wherein said first and second sites are separated from one another so that at least some amplification products in said first and second populations of amplification products have a size in the range of approximately 100–500 basepairs.

17. The method of claim 1 wherein the step of comparing comprises resolving each of said first and second populations of amplification products by gel electrophoresis and comparing the presence or level of bands of particular sizes.

18. The method of claim 1 further comprising a step of cloning individual amplification products from said first or second populations of amplification products.

19. The method of claim 1 further comprising a step of detecting a difference in the presence or level of an individual amplification product in said first population of amplification products as compared with said second population of amplification products.

20. The method of claim 19 further comprising a step of isolating an individual amplification product whose presence or level differs in said first and second populations of amplification products.

21. The method of claim 20 further comprising a step of cloning said isolated amplification product into a vector.

22. The method of claim 20 or 21 further comprising a step of screening a nucleic acid library with said isolated amplification product.

23. The method of claim 20 or 21 further comprising a step of determining the nucleotide sequence of at least a portion of said isolated amplification product.

\* \* \* \* \*

UNITED STATES PATENT AND TRADEMARK OFFICE
CERTIFICATE OF CORRECTION

PATENT NO. : 5,599,672

DATED : February 4, 1997

INVENTOR(S) : Peng Liang, Arthur B. Pardee and Cesario F. Bianchi

It is certified that error appears in the above-indentified patent and that said Letters Patent is hereby corrected as shown below:

On the cover page of the patent, please delete "[54] METHOD OF DIFFERENTIAL DISPLAY OF EXPOSED MRNA BY RT/PCR", and substitute the following therefor:

[54] METHOD OF DIFFERENTIAL DISPLAY OF EXPRESSED mRNA, BY RT/PCR

Column 5, line 63: please delete "and"; and substitute -- an -- therefor.

Column 7, line 66: please move --FIG. 1 is a schematic representation of the-- on line 67 as a new paragraph.

Column 28, line 4: please delete "1"; and substitute -- 11 -- therefor.

Column 28, line 7: please delete "1"; and substitute -- 11 -- therefor.

UNITED STATES PATENT AND TRADEMARK OFFICE
CERTIFICATE OF CORRECTION

PATENT NO. : 5,599,672
DATED : February 4, 1997
INVENTOR(S) : Peng Liang, Arthur B. Pardee and Cesario F. Bianchi It is certified that error appears in the above-indentified patent and that said Letters Patent is hereby corrected as shown below:

Column 12, line 10: please delete "rpimers", and substitute -- primers -- therefor.

Column 12, line 10: please delete "reulted" and insert -- resulted --.

Signed and Sealed this

Seventh Day of July, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

TTTTTTTTT TVN                                                                13

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:2:

TTTTTTTTT TTV                                                                13

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:3:

TTTTTTTTT VNN                                                                13

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:4:

NNTTATTNN                                                                    10

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:5:

GCTTTATTNC                                                                   10

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO (i v) ANTI-SENSE: NO (x i) SEQUENCE DESCRIPTION: SEQ ID NO:6:

NNNANNATGN    10

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i i) HYPOTHETICAL: NO (i v) ANTI-SENSE: NO (x i) SEQUENCE DESCRIPTION: SEQ ID NO:7:

NNNANNATGG    10

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i i) HYPOTHETICAL: NO (i v) ANTI-SENSE: NO (x i) SEQUENCE DESCRIPTION: SEQ ID NO:8:

GCCACCATGG    10

(2) INFORMATION FOR SEQ ID NO:9:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v i) ORIGINAL SOURCE:
        (G) CELL TYPE: Fibroblast
        (H) CELL LINE: A31

(x i) SEQUENCE DESCRIPTION: SEQ ID NO:9:

| | | | | | |
|---|---|---|---|---|---|
| CTTGATTGCC | TCCTACAGCA | GTTGCAGGCA | CCTTTAGCTG | TACCATGAAG | TTCACAGTCC | 60 |
| GGGATTGTGA | CCCTAATACT | GGAGTTCCAG | ATGAAGATGG | ATATGATGAT | GAATATGTGC | 120 |
| TGGAAGATCT | TGAGGTAACT | GTGTCTGATC | ATATTCAGAA | GATACTAAAA | CCTAACTTCG | 180 |
| CTGCTGCCTG | GGAAGAGGTG | GGAGGAGCAG | CTGCGACAGA | GCGTCCTCTT | CACAGAGGGG | 240 |
| TCCTGGGTGA | AAAAAAAAA  | | | | | 260 |

(2) INFORMATION FOR SEQ ID NO:10:

(i) SEQUENCE CHARACTERISTICS:
        (A) LENGTH: 13 base pairs
        (B) TYPE: nucleic acid
        (C) STRANDEDNESS: single
        (D) TOPOLOGY: linear ( i i i ) HYPOTHETICAL: NO ( i v ) ANTI-SENSE: NO ( x i ) SEQUENCE DESCRIPTION: SEQ ID NO:10:

TTTTTTTTTT TCA                                                                                   13

( 2 ) INFORMATION FOR SEQ ID NO:11:

( i ) SEQUENCE CHARACTERISTICS:
                ( A ) LENGTH: 10 base pairs
                ( B ) TYPE: nucleic acid
                ( C ) STRANDEDNESS: single
                ( D ) TOPOLOGY: linear ( i i i ) HYPOTHETICAL: NO ( i v ) ANTI-SENSE: NO ( x i ) SEQUENCE DESCRIPTION: SEQ ID NO:11:

GTTGATTGCC                                                                                       10

( 2 ) INFORMATION FOR SEQ ID NO:12:

( i ) SEQUENCE CHARACTERISTICS:
                ( A ) LENGTH: 10 base pairs
                ( B ) TYPE: nucleic acid
                ( C ) STRANDEDNESS: single
                ( D ) TOPOLOGY: linear ( i i i ) HYPOTHETICAL: NO ( i v ) ANTI-SENSE: NO ( x i ) SEQUENCE DESCRIPTION: SEQ ID NO:12:

GCCRCCATGG                                                                                       10

( 2 ) INFORMATION FOR SEQ ID NO:13:

( i ) SEQUENCE CHARACTERISTICS:
                ( A ) LENGTH: 10 base pairs
                ( B ) TYPE: nucleic acid
                ( C ) STRANDEDNESS: single
                ( D ) TOPOLOGY: linear ( i i i ) HYPOTHETICAL: NO ( i v ) ANTI-SENSE: NO ( x i ) SEQUENCE DESCRIPTION: SEQ ID NO:13:

AGCCAGCGAA                                                                                       10

( 2 ) INFORMATION FOR SEQ ID NO:14:

( i ) SEQUENCE CHARACTERISTICS:
                ( A ) LENGTH: 10 base pairs
                ( B ) TYPE: nucleic acid
                ( C ) STRANDEDNESS: single
                ( D ) TOPOLOGY: linear ( i i i ) HYPOTHETICAL: NO ( i v ) ANTI-SENSE: NO ( x i ) SEQUENCE DESCRIPTION: SEQ ID NO:14:

GACCGCTTGT                                                                                       10

( 2 ) INFORMATION FOR SEQ ID NO:15:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:15:

AGGTGACCGT                    10

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:16:

GGTACTCCAC                    10

( 2 ) INFORMATION FOR SEQ ID NO:17:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:17:

GTTGCGATCC                    10

( 2 ) INFORMATION FOR SEQ ID NO:18:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

GCCGCCATGG CTCTGAAGAG AATCCACAAG GACACCCATG AA                    42

( 2 ) INFORMATION FOR SEQ ID NO:19:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

```
GTTGCATTTA CAACAAGAAT TTATCATCCA AATATTAACA GTAATGGCAG CATTTGTCTT        60
GATATTCTAC GGTCACCT                                                      78
```

( 2 ) INFORMATION FOR SEQ ID NO:20:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:20:

```
GTAYGCNTGT                                                               10
```

( 2 ) INFORMATION FOR SEQ ID NO:21:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:21:

```
GTAYGCNTGC                                                               10
```

( 2 ) INFORMATION FOR SEQ ID NO:22:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:22:

```
GTAYGCNTGC                                                               10
```

( 2 ) INFORMATION FOR SEQ ID NO:23:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:23:

```
GTATGCNTGT                                                               10
```

( 2 ) INFORMATION FOR SEQ ID NO:24:

( i ) SEQUENCE CHARACTERISTICS:

```
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:24:

GTACGCNTGT                                                                    10

( 2 ) INFORMATION FOR SEQ ID NO:25:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:25:

GTATGCNTGC                                                                    10

( 2 ) INFORMATION FOR SEQ ID NO:26:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:26:

GTACGCNTGC                                                                    10

( 2 ) INFORMATION FOR SEQ ID NO:27:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

NNNRNNATGN                                                                    10
```